United States Patent [19]
Essinger, Jr.

[11] Patent Number: 5,665,678
[45] Date of Patent: Sep. 9, 1997

[54] COMPOSITIONS AND SUSPENSION CONTAINING A LOW-MELTING TEMPERATURE PESTICIDE

[75] Inventor: James Franklin Essinger, Jr., Ballwin, Mo.

[73] Assignee: Monsanto Company, St. Louis, Mo.

[21] Appl. No.: 456,260

[22] Filed: May 31, 1995

Related U.S. Application Data

[62] Division of Ser. No. 223,334, Apr. 5, 1994.

[51] Int. Cl.$^6$ .................................. A01N 25/22
[52] U.S. Cl. .................. 504/116; 504/175; 504/211; 504/234; 504/254; 504/265; 504/270; 504/262; 504/307; 504/319; 504/323; 504/330; 504/342; 504/355; 504/244; 71/DIG. 1
[58] Field of Search .................. 504/116, 244, 504/195, 211, 234, 254, 262, 265, 270, 307, 319, 323, 330, 342, 355; 71/DIG. 1

[56] References Cited

U.S. PATENT DOCUMENTS 2,913,372  11/1959  Velde et al. ..................... 167/42

FOREIGN PATENT DOCUMENTS

| 0 213 328 | 3/1987 | European Pat. Off. | A01N 25/12 |
| 0 494 386 A1 | 5/1992 | European Pat. Off. | A01N 37/02 |
| 9007272 | 7/1990 | WIPO . | |

*Primary Examiner*—Richard L. Raymond
*Assistant Examiner*—Brian G. Bembenick
*Attorney, Agent, or Firm*—Stanley M. Tartar; Arnold, White & Durkee

[57] ABSTRACT

Agriculturally acceptable pesticidally active ingredients, such as herbicides, fungicides, and insecticides of low melting point, typically in the range from about 30° C. to about 130° C. and preferably in the range from about 30° C. to about 90° C. and low water solubility, typically in the range from about 0.01 ppm to about 1000 ppm and preferably in the range from about 0.01 ppm to about 300 ppm are frequently formulated as water-dispersed agrichemically acceptable formulations such as wettable powders (WP), water-dispersible granules (WG), and suspension concentrates (SC) and the like.

39 Claims, 7 Drawing Sheets

COMPOSITIONS AND SUSPENSION CONTAINING A LOW-MELTING TEMPERATURE PESTICIDE

This application is a divisional of U.S. Ser. No. 08/223,334 filed Apr. 5, 1994, now pending.

Agriculturally acceptable pesticidally active ingredients and mixtures thereof, such as herbicides, fungicides, and insecticides of low melting point, typically having a melting point in the range from about 30° C. to about 130° C. and preferably in the range from about 30° C. to about 90° C. (at normal atmospheric pressure) and low water solubility, typically in the range from about 0.01 ppm to about 1000 ppm and preferably in the range from about 0.01 ppm to about 300 ppm are formulated using this invention as water-dispersed formulations such as wettable powders (WP), water-dispersible granules (WG), and suspension concentrates (SC). Nonlimiting examples of acceptable low melting point pesticidal actives which can be used in this invention are found in families of pyridines, nitroanilines, acetanilides, organophosphates, triazines, pyrethroids, isoxazolidinones, carbamates, benzoxazoles, substituted phenoxys, substituted ureas, triazoles, oxadiazolinones, imidazolinones and azoryl chemistries, mixtures there of and the like.

Aging stability and suspensability (comparable to commercial formulation standards) of WP, WG, and SC formulations requires a small dispersed particle size (e.g. 2–20 μm mean size) containing the pesticidally active ingredient. Achieving this rather small particle size may require formulation particle size reduction (e.g. grinding), by hammermill, media mill, air mill, and combinations thereof and the like.

Due to the rather low melting temperature of the pesticide active preferably utilized in this invention, typically less than about 90° C. at normal atmospheric pressure, direct grinding (as in the art) of the discrete solid pesticide active can be difficult due to melting or softening of the pesticide active itself during that grinding. One possible remedy, cryogenic grinding, is an option which may work, but with added undesirable processing expense which makes it unattractive and may not overcome resulting aging problems with the formulation.

Alternatively the pesticide active may be intentionally heated in a suitable container to a liquid melt physical state and then absorbed into a relatively rigid, porous, powder carrier, such as precipitated silica or the like to provide improved grinding characteristics of that composition versus grinding of the discrete solid pesticide active. These improved grinding characteristics assume that the once liquid active has crystallized inside the porous powder carrier particles to allow such grinding.

If however the crystallization rate of the above described process is too slow as happens using this absorption-grinding technique then this absorption method may not be practical. Without being bound by theory, it is believed that slow crystallization can be due to factors including high viscosity in the supercooled liquid active, lack of seed surface to initiate crystallization, low crystallization energy, etc. Supercooling, i.e. a cooling below the normal freezing point of a liquid without solidification or crystallization occurring immediately, is a common tendency of many pesticide active ingredients.

Surprisingly, in the process of this invention, a quite different family of nucleating agents was discovered to provide effective nucleation of a supercooled pesticide active (or a mixture of pesticide actives), and subsequent rapid crystallization of the pesticide active, for practical preparation of WP, WG, SC, etc. formulation types from molten, low-melting point pesticide active ingredients. In carrying out the process of this invention, active ingredient crystallization is much more rapid, thorough, and predictable; otherwise, preparation of a water dispersible formulation from a low melting pesticide active will be too slow economically, or is likely to be poor quality.

OBJECTS OF THE INVENTION

It is an objective of the invention to provide an improved process in preparing a water dispersible formulation from a low melting pesticide active technical material.

Further, it is an objective of the invention to provide an enhanced process for preparing a dry, powder pesticidally active composition which enables rapid crystallization of liquid technical in a carrier in the composition.

It is yet another objective of this invention to provide a water dispersible agriculturally acceptable composition which may be rapidly dispersed in water, which contains a low melt pesticide active.

These objects as well as other objects and advantages of the present invention will become apparent to those skilled in the art from the following detailed description.

SUMMARY OF THE INVENTION

This invention comprises a practical method for preparing an enhanced agriculturally acceptable stable water dispersible formulation of a low-melting temperature active ingredient in which a compound selected from the group consisting of carboxylic acids, esters, and amides, having melting point range of 30° C.–130° C. and having a chain length of about 3 to about 30 carbon atoms and preferably from about 5 carbon atoms to about 22 carbon atoms, is formulated to provide the enhanced inventive formulation which comprises the steps of:

a. admixing a low melt pesticide active(s) with a porous carrier, which preferably has been warmed to a temperature in the range from about 30° C. to about 130° C., preferably in the range from about 30° C. to about 90° C. to form a dry intermediate powder wherein the pesticide active has been absorbed as a liquid, b. admixing with said dry intermediate powder, a nucleating agent selected from the above group to form a dry powder formulation intermediate, c. cooling said dry powder formulation intermediate and admixing therewith various functional ingredients to provide a dry or liquid formulation having commercial formulation characteristics, and d. grinding said dry or liquid formulation to achieve desired dispersion particle size whereby the formulation of this invention is prepared.

Granulation to make a dry formulation is an option.

Another embodiment comprises a practical method for preparing an enhanced agriculturally acceptable stable water dispersible formulation of a low-melting temperature active ingredient in which a compound selected from the group consisting of carboxylic acids, esters, and amides, having melting point range of 30°–130° C. and having a chain length of 5 to 22 carbon atoms, is formulated therewith to provide this enhanced formulation which comprises the steps of:

a. admixing said nucleating agent selected from the above group with a pesticide active to form a premix, b. admixing said premix with a porous carrier which is at a temperature in the range from about 30° C. to about 130° C., preferably from about 30° C. to about 90° C. to form a dry, powder, formulation intermediate wherein the pesticide active has been absorbed as a liquid, c. cooling said dry powder formulation intermediate and admixing therewith various functional ingredients to provide for commercial formulation characteristics, and d. grinding said formulation to achieve desired dispersion particle size whereby a dry or liquid formulation of this invention is prepared.

DETAILED DESCRIPTION OF THE INVENTION

This invention comprises a method for preparing an enhanced agriculturally stable acceptable water dispersible formulation of low melting temperature pesticide active (ingredient) in which a compound selected from the group consisting of carboxylic acids, esters, and amides, having melting point range of 30° C.–130° C. and a chain length of about 3 to about 30 carbon atoms and preferably about 5 to about 22 carbon atoms or mixtures thereof, are formulated to provide an enhanced water dispersible formulation containing said pesticide active which comprises the steps of a. admixing a low melt pesticide active with a porous carrier which has been warmed to a temperature in the range from about 30° C. to about 130° C., preferably from about 30° C. to about 90° C. to form a dry intermediate powder wherein the pesticide active has been absorbed as a liquid, b. admixing with said dry intermediate powder, a nucleating agent selected from the above group to form a dry, powder formulation intermediate, c. cooling said dry powder formulation intermediate and admixing therewith various functional ingredients to provide a dry or liquid formulation having commercial formulation characteristics and thereafter d. grinding said dry or liquid formulation to achieve desired dispersion particle size whereby the formulation of this invention is prepared.

Using conventional granulation means thereafter to prepare a dry formulation is an option.

Another embodiment comprises a practical method for preparing an enhanced agriculturally stable acceptable water dispersible formulation of a low-melting temperature active ingredient in which a nucleating agent selected from the group consisting of carboxylic acids, behenic acid methyl ester, and amides, having melting point range of 30°–130° C. and having a chain length of about 3 to 30 carbon atoms and preferably about 5 to about 22 carbon atoms or mixtures thereof, is formulated therewith to provide an enhanced dispersible agricultural formulation which comprises the steps of:

a. admixing said nucleating agent selected from the above group with a pesticidal active to form a premix, b. admixing said premix with a porous carrier which is at a temperature in the range from about 30° C. to about 130° C., preferably from about 30° C. to about 90° C. to form a dry, powder, formulation intermediate wherein the pesticide active has been absorbed as a liquid, c. cooling said dry powder formulation intermediate and admixing therewith various functional ingredients to provide for commercial formulation characteristics, and d. grinding said formulation to achieve desired dispersion particle size whereby a dry or liquid formulation of this invention containing said pesticide active is prepared.

Warming of the porous carrier to the desired temperature is preferably done first.

Typical pesticide active ingredients of low melting point, and low water solubility, which are frequently formulated as water-dispersed formulations such as wettable powders (WP), water-dispersible granules (WG), and suspension concentrates (SC) include acetanilides, nitroanilines, pyridines, organo-phosphates, triazines, pyrethroids, isoazolidinones, carbamates, benzoxazoles, substituted phenoxys, substituted ureas, triazoles, oxadiazolinones, imidazolinones, azoryls and more particularly include alachlor, trifluralin, dithiopyr, chlorpyrifos, ametryn, bifenthrin, clomazone, triallate, fenoxaprop-ethyl, diclofop-methyl, fenoxycarb, thiazopyr, oxyflurofen, linuron, imibenconazole, and oxadiazon. Mixtures thereof and the like of pesticide actives maybe employed in this invention.

The above pesticide actives are readily available, for example, alachlor, dithiopyr and triallate from Monsanto Company, trifluralin from Dow Elanco, chlorpyrifos from Dow Elanco, ametryn from Ciba-Geigy, bifenthrin and clomazone from FMC Corporation, fenoxaprop-ethyl and diclofo-methyl from Hoechst-Roessel, fenoxycarb from Ciba Geigy, thiazopyr from Monsanto, oxyflurofen from Rohm and Haas, linuron from DuPont, imibenconazole from Hokko Chemical Industry Co and oxadiazon from Rhone Poulenc.

Illustrative carboxylic acids useful in this invention include glutaric acid, myristic acid, stearic acid, mixtures thereof and of the like. Stearic acid is a preferred carboxylic acid.

A particularly useful amide is stearamide.

Various functional ingredients useful in this invention include water, alkylsulfate salts, lignosulfonates, naphthalene sulfonates, polyvinylpyrrolidones, propylene glycol, biocides (e.g. Proxel), xanthan gums, ethoxylated siloxanes or alkylphenols, quaternary alkyl ammonium salts, mixtures thereof and the like.

Mixtures of various carboxylic acid, esters and amides may be employed as nucleating agents in this invention.

The term "low melting point" as used herein means having a melting point in the range from about 30° C. to about 30° C. and preferably from about 30° C. to about 90° C. although greater or less temperatures may be used.

Suitable nonlimiting examples of carrier materials include inorganic carrier materials precipitated silica or clay powder. Other suitable carrier material which may be employed include, but are not limited to porous organopolymeric powders, such as polystyrene.

Inorganic or clay-type carriers useful herein can be obtained from the J. M. Huber Corporation in Macon, Ga., such as Zeolex 7 or Hubersorb 600, although other clays and mixtures may be utilized.

A useful precipitated silica may be obtained from PPG Industries, Pittsburgh, Pa. as HiSil ABS or from Degussa as Wessalon 50 although other substantially equivalent silicas and mixtures thereof may be utilized.

A useful stearic acid may be obtained from Witco Corporation in Memphis, Tenn. as Hystrene 9718 although other stearic acids and mixtures thereof may be utilized.

Without being bound by theory it is believed that effective nucleation of the supercooled active, and subsequent rapid crystallization of the active, are important in this invention for practical preparation of WP, WG, SC, etc. formulation types from molten, low-melting point active ingredients. Crystallization needs to be fairly rapid, thorough, and predictable; otherwise, formulation preparation will be too slow economically, or of poor quality.

The term "stable" as used herein means meeting or exceeding the performance under test of commercial standard formulations at ambient storage temperature with respect to formulation homogeneity, dispersability and sprayability.

The term "commercial formulation characteristics" as used herein means that the formulation of this invention is commercially compatible with current storage, handling and application practices of the intended user.

The term "rapid" as used herein means formation of a definite active ingredient crystal state in a time of less than about 5 hours and preferably less than about 3 hours.

Illustratively crystallization begins when the nucleating agent is crystalline and is in contact with supercooled, active ingredient.

Illustratively crystallization ends when the supercooled liquid active ingredient has become a crystalline solid.

The term "cooling" as used herein means cause or allow to cool so that pesticide active crystallization may proceed.

In the process of this invention which is classified as an absorption formulating method, the nucleating agent is chemically different from the active ingredient, i.e. crystallization is due to heterogeneous nucleation. [In contrast, homogeneous nucleation is commonly practiced by addition of solid active ingredient to a supercooled or super-saturated liquid containing the same pesticide active. It is believed that the solid pesticide active ingredient particles provide the surface (nuclei) for the liquid (containing the same active ingredient) to crystallize on.] For the method herein, the class of nucleating agents are chemically quite different from actives for which faster crystallization was detected.

An absorption formulating method utilizes absorption of the liquid active ingredient into a porous carrier as an essential step in quality formulation preparation.

Without being bound by theory, the process of this invention works surprisingly well by providing a seed surface for crystallization, and may be generally called heterogeneous nucleation. The nucleating agents are preferably chemically quite different from the active. The nucleating agent can be either pre-mixed with a pesticide active (ingredient) prior to absorption into the porous carrier, or, if the nucleating agent melts at a convenient temperature, it can be absorbed as a separate molten ingredient. Once the absorption process is finished, and a loaded powder intermediate composition of carrier and active and nucleating agent is allowed to cool, the nucleating agent provides a surface to enhance the crystallization rate of the now supercooled liquid active ingredient. Crystallization of this matrix improves grindability, and resistance to active ingredient migration upon contact of the loaded powder with water. Low cost porous carriers are frequently hydrophilic; dispersion of the loaded powder in water with still-liquid active can result in displacement of the active ingredient from the carrier by water, a mode of formulation failure. Of course, WP and WG formulations are dispersed in water during quality analysis, and by the end use customer. Also, dispersion of solids in water occurs during the SC formulating. Therefore, the loaded powder must be readily compatible with water contact.

In practicing the process of this invention, selection of compounds for nucleation of active ingredients is typically based on visual comparison of crystallization rates for side-by-side samples and/or comparison of Differential Scanning Calorimetry (DSC) plots for active alone, versus active and about 5 wt. % candidate nucleating agent. The utility of these two tests, for ranking candidate nucleating agent effectiveness, was initially determined by the later observed correlation with this surprising sequence of observations with the pesticide active dithiopyr:

1. From the hot melt state, a dithiopyr bulk sample crystallized slowly over about one day at 20° C. Subambient cooling of the melt did not accelerate crystallization possibly due to viscosity. This indicated potential difficulties in preparing a water-dispersible formulation from dithiopyr melt since a major component of the formulation (dithiopyr) may remain liquid for greater than or about one day and could migrate, causing formulation failure.

2. A water-dispersible formulation precursor (loaded powder) was prepared by mixing 49 wt % PPG Hisil T-700 precipitated silica with 51 wt % dithiopyr technical melt at about 70° C. (Dithiopyr technical melts at about 55° C.) Cooled the loaded powder to about 20° C. and let stand for about 2 hours and dispersed this loaded powder in water. Observed white silica solids and gold-colored particles of dithiopyr technical formed immediately in the dispersion. This result showed that the dithiopyr was still liquid in the silica particles, was displaced by water, and congealed in the aqueous phase.

3. Observation test #2 above was repeated, but by mixing 45% T-700, 52% technical and 3% stearic acid. Cooled the loaded powder to about 40° C. and immediately dispersed in water. Only white particles were seen, no gold-colored particles. This small proportion of stearic acid had an immediate effect; technical was not displaced upon mixing loaded powder with water.

4. Observation test #2 above was repeated, but by mixing 88% T-700 and 12% technical. Cooled the loaded powder to about 20° C. and held for 2 days total. With periodic dispersion tests in water, gold-color particles of dithiopyr occurred each time. After 2 days storage, technical was still being displaced by water, and was apparently still a supercooled liquid in the silica particles, without stearic acid use.

As shown below in Examples 1 and 2, the following two methods, for evaluation of candidate nucleating agents, provided valuable insight and correlation with observations 1–4 above.

Crystallization Rate Visual Comparison

To one ounce flint glass B/R bottle from Fisher Scientific, add about 11.5 grams liquid active ingredient and about 0.5 grams candidate nucleating agent. Place all capped bottles in oven to equilibrate temperature; active ingredient portion is liquid in all bottles; candidate agent may be liquid or solid depending on the selection. Bottles are placed at about 20° C. side-by-side for cool-down and visual observations. Samples typically progress through the sequence: (1) flowable, (2) non-flowable and translucent, (3) non-flowable and opaque (which here defines the comparative crystallization time). The non-flowable and translucent state occurs when the candidate nucleating agent is crystalline but the active ingredient is not, and as such is not indicative of the active ingredient crystallization rate. Upon achieving the opaque state, all samples are ranked on a time-to-achieve basis.

Differential Scanning Calorimetry (DSC) Analysis

Prior to DSC analysis, samples are pre-heated to where the active is liquid. Sample is sealed in aluminum pan and held in DSC for 10 minutes above the active melt temperature. The sample is cooled to –60° C. at –2° C./minute, and finally heated back to the original temperature at +2° C./minute. This procedure was established to generally follow the practice of absorbing the active as a liquid into a porous carrier and then cooling toward about 20° C. for crystallization. Critical information from the DSC plots includes endotherm and exotherm temperature correlation and energy balance.

(Note—The same lot of an active ingredient is used throughout the Examples.)

EXAMPLE 1

Crystallization Rate Visual Comparison: Dithiopyr Technical Mixtures

To each of twenty-two bottles was added 11.7+0.3 grams of dithiopyr technical (same lot) as a hot, liquid melt. Twenty-one potential nucleating agents were added at 0.52±0.2 grams to these bottles as shown:

| Bottle # | Agent | literature melting point ~°C. for agent |
|---|---|---|
| 1 | glycerol monostearate flake | 58 |
| 2 | sodium lauryl sulfate powder | 205 |
| 3 | stearic acid flake | 65 |
| 4 | polyethylene glycol 8000 powder | 62 |
| 5 | none (dithiopyr technical only) | no agent |
| 6 | Witco Morwet EFW powder | no data |
| 7 | behenic acid, methyl ester powder | 54 |
| 8 | oleic acid liquid | 13 |
| 9 | lauric acid powder | 45 |
| 10 | dodecanedioic acid powder | 129 |
| 11 | myristic acid flake | 52 |
| 12 | palmitic acid flake | 59 |
| 13 | behenic acid flake | 69 |
| 14 | stearamide powder | 103 |
| 15 | oleamide powder | 73 |
| 16 | stearyl erucamide powder | 74 |
| 17 | PPG Hisil ABS precipitated silica powder | no data |
| 18 | glutaric acid powder | 97 |
| 19 | phthalic acid powder | 210 |
| 20 | malonic acid powder | 136 |
| 21 | poly(acrylic acid) powder, ave. molecular weight = 2000 | no data |
| 22 | poly(methyl methacrylate) powder, average molecular weight | 180 |

Bottles were capped and placed in oven at 75° C. until the physical state has stabilized (i.e. 100% liquid, or liquid technical+solid agent), taking 1–2 hours. Bottles were removed from oven and placed side-by-side at room temperature (~23° C.). Changes of state are detected by slight tipping of the bottles and visual inspection, versus time. Endpoint was defined as time to achieve 100% visually-opaque solid. Results were:

| Bottle # | Agent state at startpoint | time-to-endpoint hours | relative crystallization rate, 1.0 = highest | Agent Type |
|---|---|---|---|---|
| 1 | liquid | ~20 | ~0.03 | C18 ester |
| 2 | solid | ~20 | ~0.03 | C12 sulfate |
| 3 | liquid | 2.5 | 0.30 | C18 acid |
| 4 | liquid | ~20 | ~0.03 | polyether |
| 5 | no agent | ~20 | ~0.03 | — |
| 6 | solid | ~20 | ~0.03 | anionic |
| 7 | liquid | 2.0 | 0.38 | C20–22 ester |
| 8 | liquid | ~20 | ~0.03 | C18 ene acid |
| 9 | liquid | ~20 | ~0.03 | C12 acid |
| 10 | solid | 0.75 | 1.0 | C12 diacid |
| 11 | liquid | 1.25 | 0.60 | C14 acid |
| 12 | liquid | 4.0 | 0.19 | C16 acid |

-continued

| Bottle # | Agent state at startpoint | time-to-endpoint hours | relative crystallization rate, 1.0 = highest | Agent Type |
|---|---|---|---|---|
| 13 | liquid | 5.0 | 0.15 | C20–22 acid |
| 14 | solid | 1.5 | 0.50 | C18 amide |
| 15 | liquid | 7 | 0.11 | C18 ene amide |
| 16 | liquid | 7 | 0.11 | C18 ester |
| 17 | solid | ~20 | ~0.03 | silica |
| 18 | solid | 1.5 | 0.5 | C5 diacid |
| 19 | solid | ~20 | ~0.03 | aryl diacid |
| 20 | solid | ~20 | ~0.03 | C3 diacid |
| 21 | solid | ~20 | ~0.03 | poly alkyl acid |
| 22 | solid | ~20 | ~0.03 | poly alkyl ester |

This data identified C5 diacid, C12 diacid, C14 monoacid, C16 monoacid, C18 monoacid, C18 amide, C20–22 monoacid, and C20–22 ester as effective nucleating agents, the dithiopyr portion crystallizing 17×, 30×, 20×, 5×, 10×, 17×, 4×, and 13× faster than dithiopyr technical alone (Bottle #5), respectively. The remaining samples crystallized slightly to negligibly faster than technical alone. The C14 acid, C18 acid, and C20–22 ester are preferred practical candidates for dithiopyr rapid crystallization since these are also liquids near the dithiopyr melt temperature, allowing incorporation as liquids for more intimate contact with dithiopyr technical. The crystallization sensitivity of dithiopyr to these eight compounds is surprising, considering that dithiopyr is a chemically unrelated pyridine compound. As used herein, C18 means chain length of 18 carbon atoms, Acid means carboxylic acid, and Ene means alkene functionality.

This result was taken to imply that the lack of dithiopyr displacement by water from the loaded powder described above in the observation tests, was due to stearic acid causing dithiopyr to crystallize prior to dispersing the loaded powder in water.

EXAMPLE 2

DSC Analysis: Dithiopyr Technical Mixtures

Since Example 1 identified stearic acid as enhancing technical crystallization rate by ten-fold, this difference should be detectable by DSC.

Figure 1:
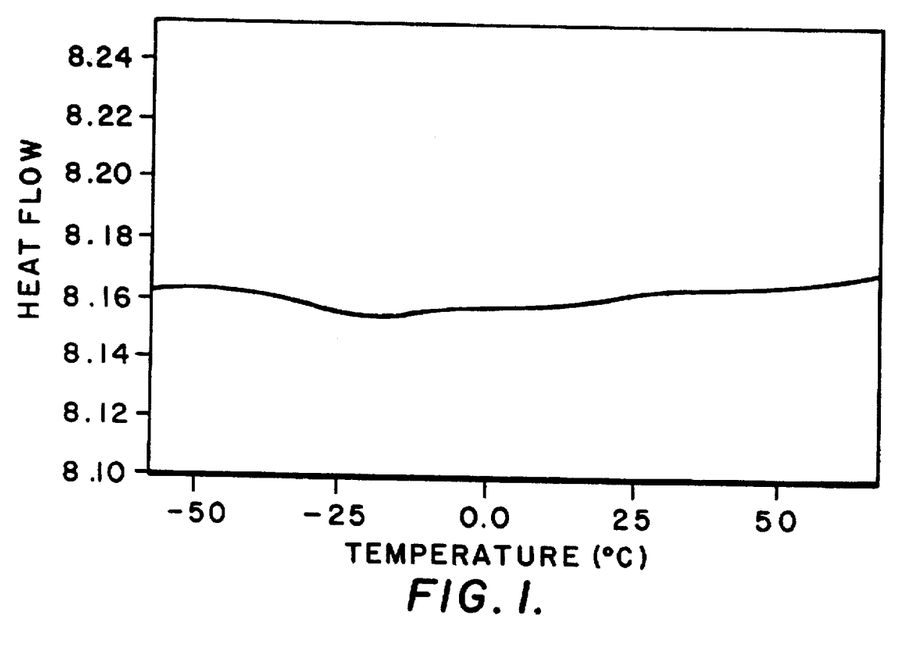
FIG. 1 Shows that molten dithiopyr technical did not crystallize upon cooling to –60° C.
Figure 2:
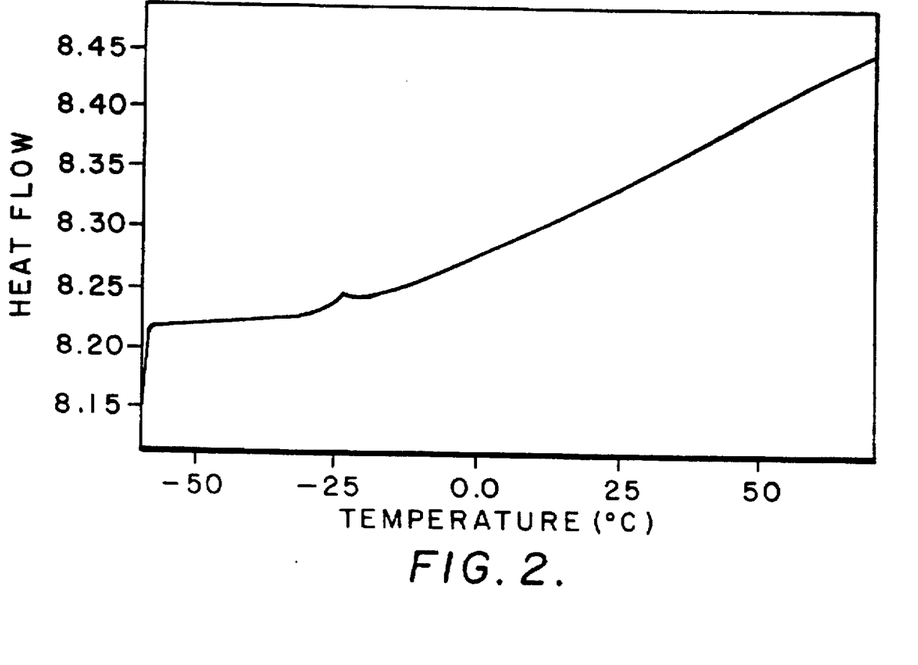
FIG. 2 Shows that dithiopyr technical did not crystallize or melt upon warming to 70° C.
Figure 3:
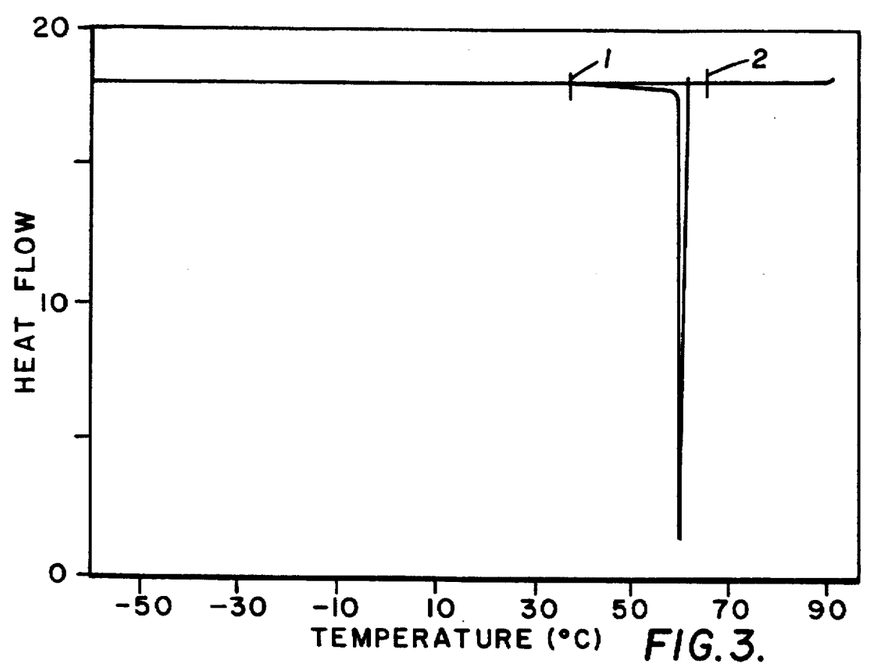
FIG. 3 Shows that molten stearic acid crystallizes readily at about 60° C. upon cooling.
Figure 4:
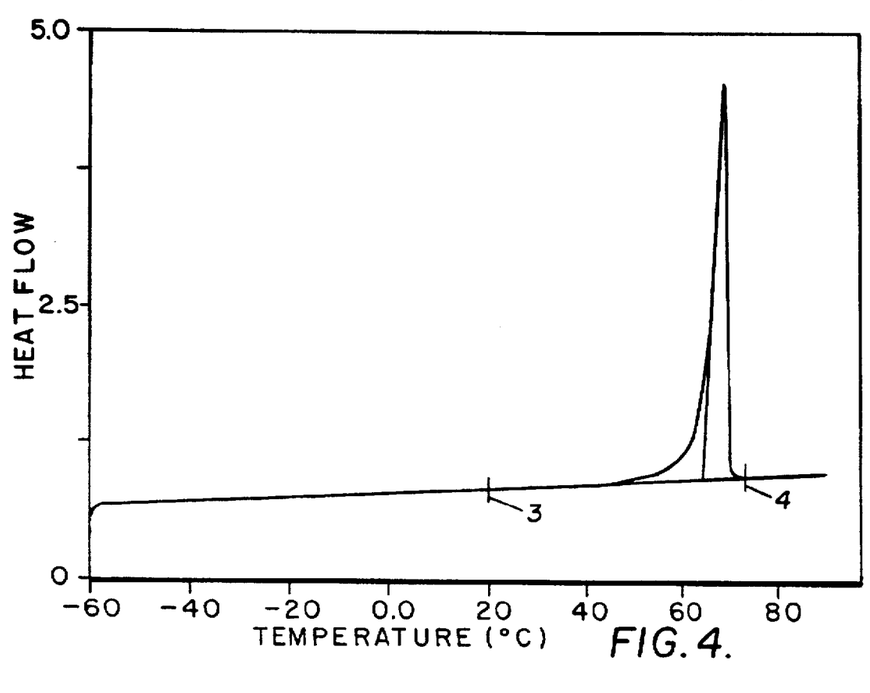
FIG. 4. Shows that crystalline stearic acid melted as expected at about 65° C.
Figure 5:
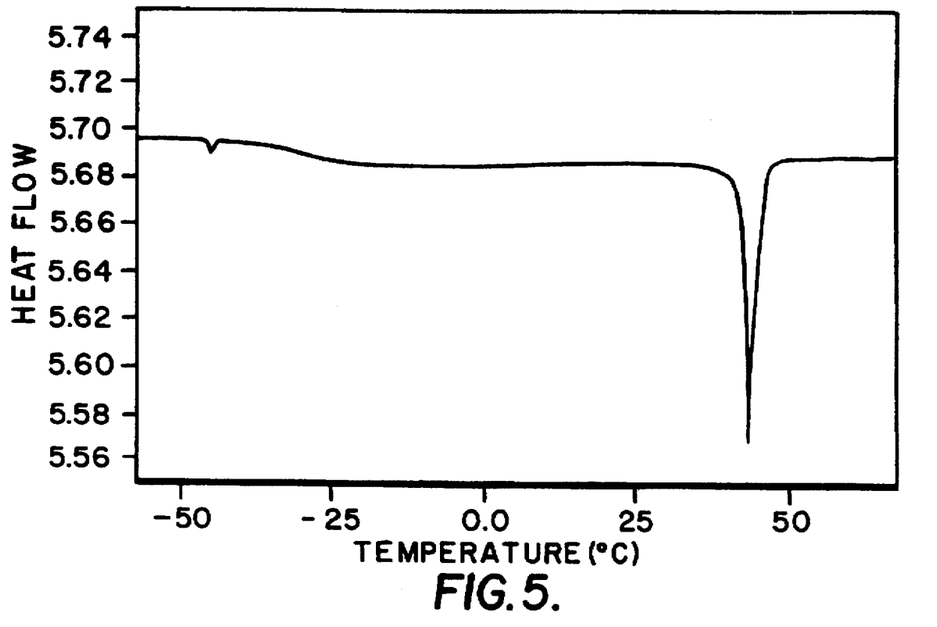
FIG. 5. Shows that the 4.3% stearic acid portion of a molten mixture with dithiopyr crystallized at about 45° C. Crystallization of dithiopyr was not apparent.
Figure 6:
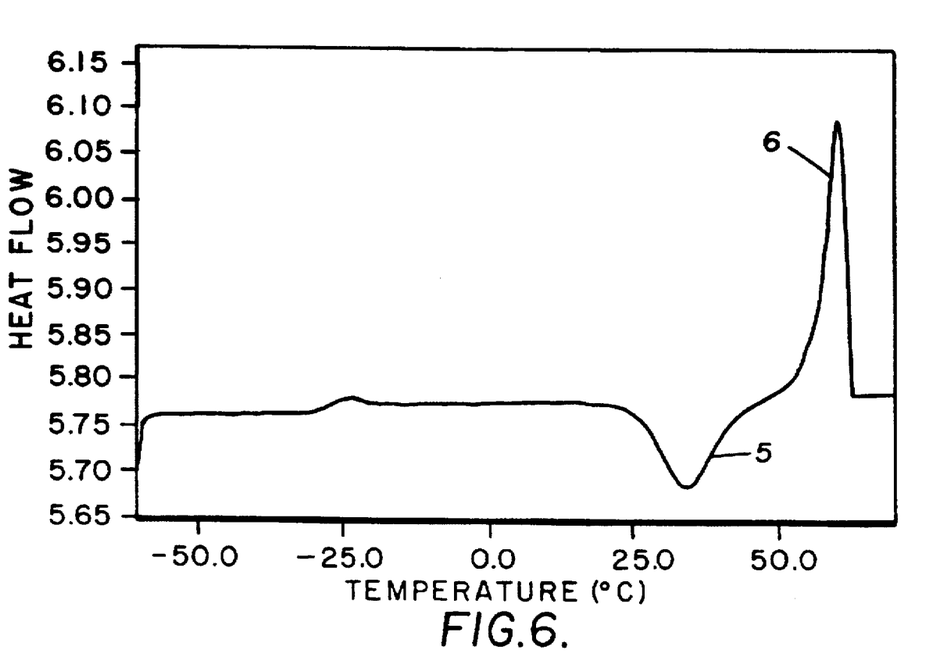
FIG. 6 Shows that when a mixture of supercooled dithiopyr and crystalline stearic acid is heated, dithiopyr crystallized at about 25° C., followed by dithiopyr and stearic acid melting at about 56° C.

Three samples were run:

1. Sample Bottle #5, dithiopyr technical, above
2. stearic acid alone
3. Sample Bottle #3, ~96% technical+~4% stearic acid Results:

1. Technical did not crystallize upon cooling from +70° C. to −60° C. Upon reheating, the most notable detail was a −25° C. glass transition (Tg). Since technical melting point is ~55° C., supercooling is apparent. See FIG. 1 and FIG. 2.
2. Stearic acid exhibited predicted crystallizing and melting transitions at 60°–65° C. The energy values of 49–50 calories/gram closely match literature values. No supercooling tendency seen. See FIG. 3 and FIG. 4.
3. Cool-down scan integration suggested that stearic acid portion has crystallized, but technical portion is supercooled. However, during heat-up, the plot suggested that technical crystallizes at room temperature, and then both melt similar to a single component. During cool-down, apparently the viscosity of supercooled dithiopyr increased too rapidly to allow dithiopyr crystallization. But, during heat-up, with time and less viscous technical, crystallization rapidly occurred in the presence of stearic acid crystals. See FIG. 5 and FIG. 6.

This data showed that stearic acid crystals will nucleate supercooled dithiopyr technical, causing dithiopyr crystallization.

EXAMPLE 3

Crystallization Rate Visual Comparison: Trifluralin Technical Mixtures

To each of three glass bottles, added trifluralin technical. Potential nucleating agents added to bottles were stearic acid, methyl behenate, and none (control), respectively. Place capped bottles in 75° C. for 2 hours. Remove bottles, shake, and place side-by-side at about 23° C. for visual observation. Crystallization endpoint reached in 1 hour, >67 hours, and >67 hours, respectively.

Here, trifluralin technical was nucleated by a select compound from the above group, stearic acid, causing trifluralin crystallization.

EXAMPLE 4

DSC Analysis: Trifluralin Technical Mixtures

Figure 7:
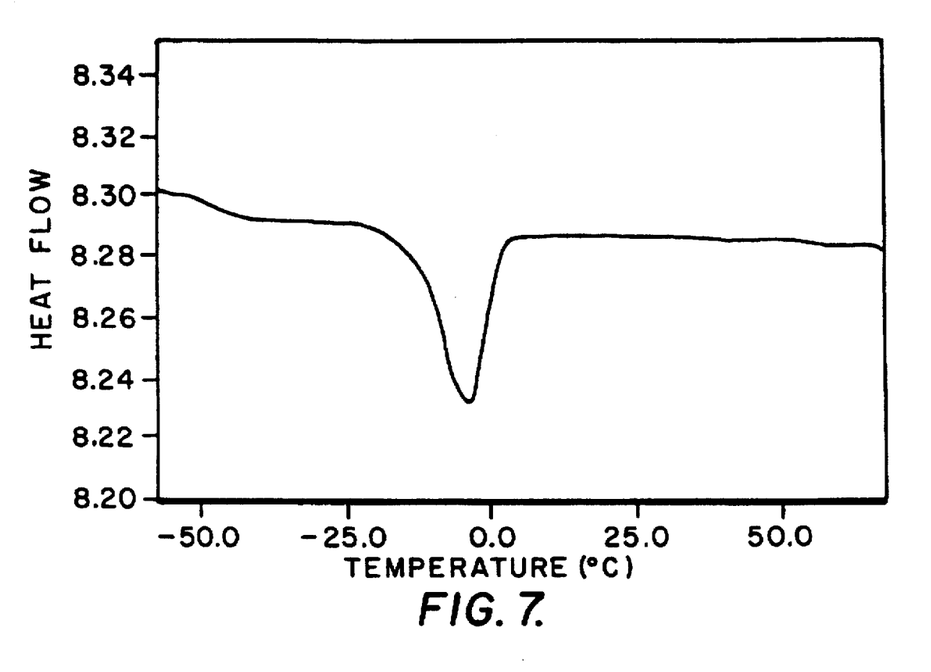
FIG. 7 Shows molten trifluralin partially crystallizing at about 0° C.
Figure 8:
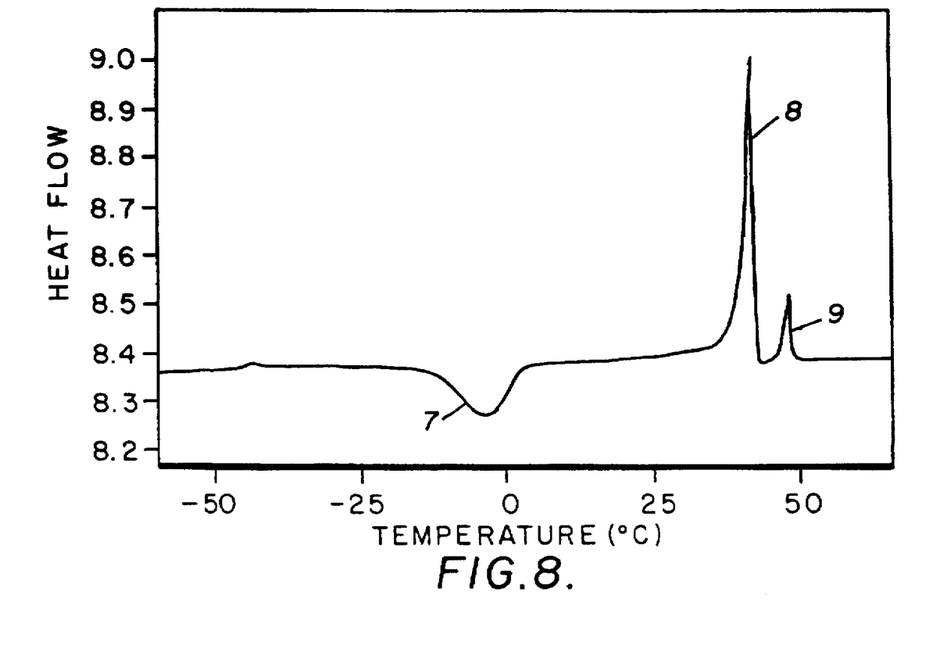
FIG. 8 Shows remainder of trifluralin crystallizing at about –12° C., and then two crystal types melting at about 40° C. and about 47° C.
Figure 9:
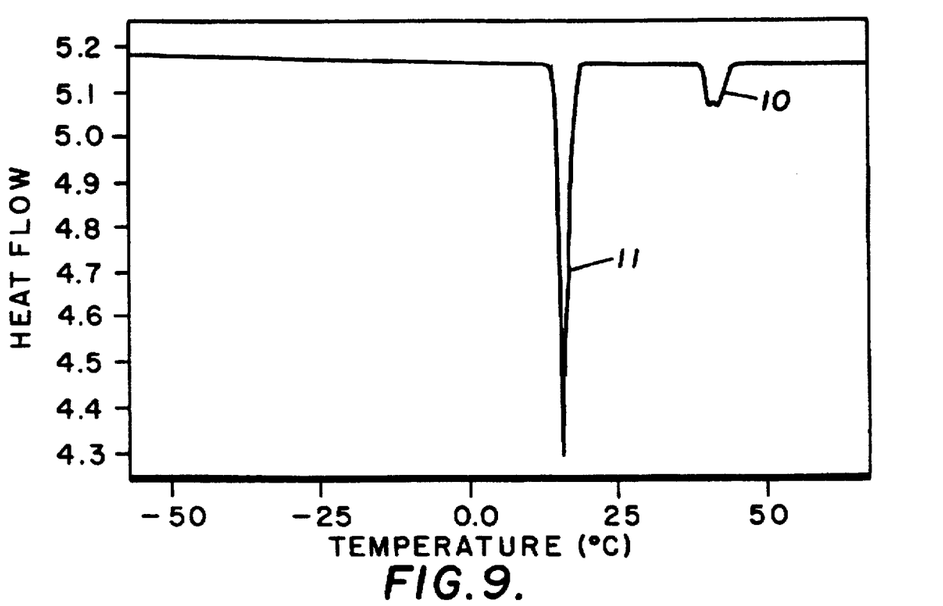
FIG. 9 Shows that the 4.8% stearic acid portion of a molten mixture with trifluralin crystallized at about 43° C., followed by complete crystallization of trifluralin at about 17° C.
Figure 10:
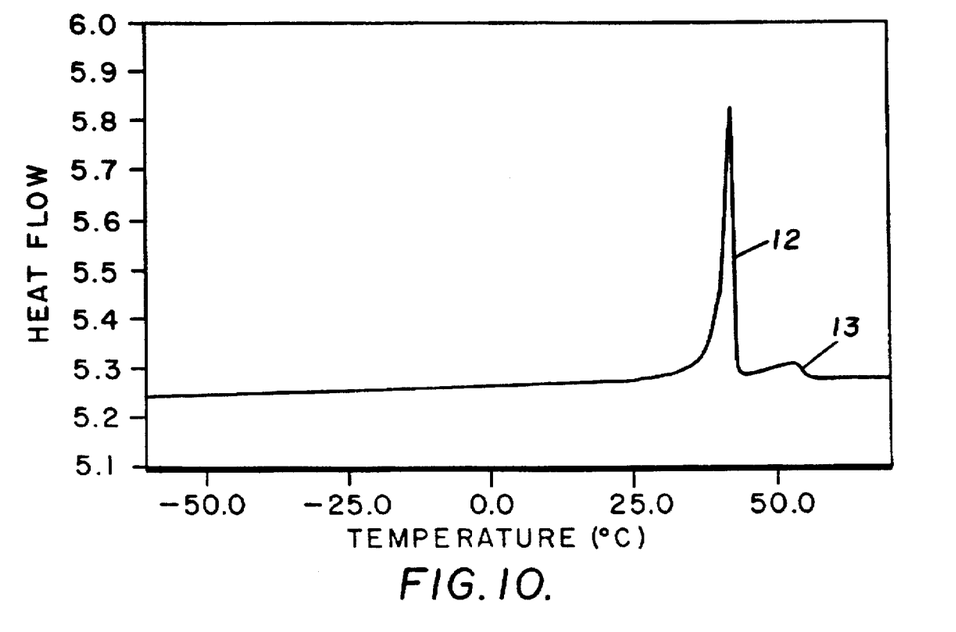
FIG. 10 Shows crystalline mixture of trifluralin and stearic acid melting at about 40° C. and about 47° C., respectively.

Since Example 3 identified stearic acid as a nucleating agent for supercooled trifluralin, DSC should detect differences. Two samples were run:

1. trifluralin technical alone
2. trifluralin technical with 4.8% by weight stearic acid Results:

1. Technical partially crystallized at ~0° C. on cool-down, and finished crystallizing on heat-up at ~0° C. See FIG. 7 and FIG. 8.
2. Stearic acid crystallized, followed by Technical completely crystallizing at ~17° C. on cool-down. See FIG. 9 and FIG. 10.

Here, stearic acid nucleated supercooled trifluralin technical, causing trifluralin crystallization.

EXAMPLE 5

DSC Analysis: Alachlor Technical Mixtures Two samples were run:

1. alachlor technical alone
2. alachlor technical with 5% stearic acid

Figure 11:
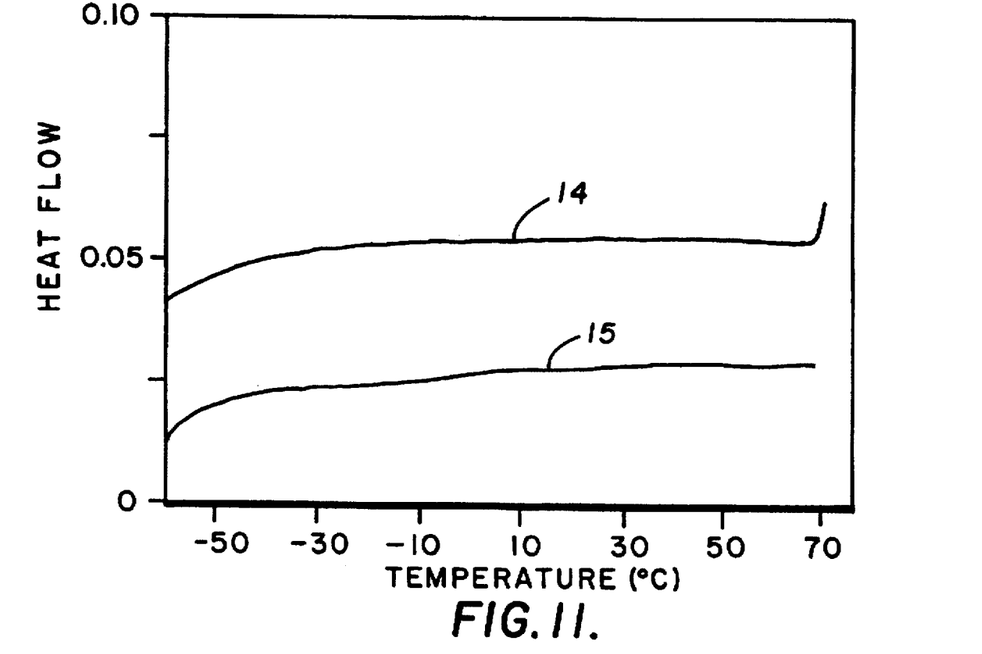
FIG. 11 Shows that molten alachlor technical did not crystallize or melt upon cooling to –60° C. and then reheating.
Figure 12:
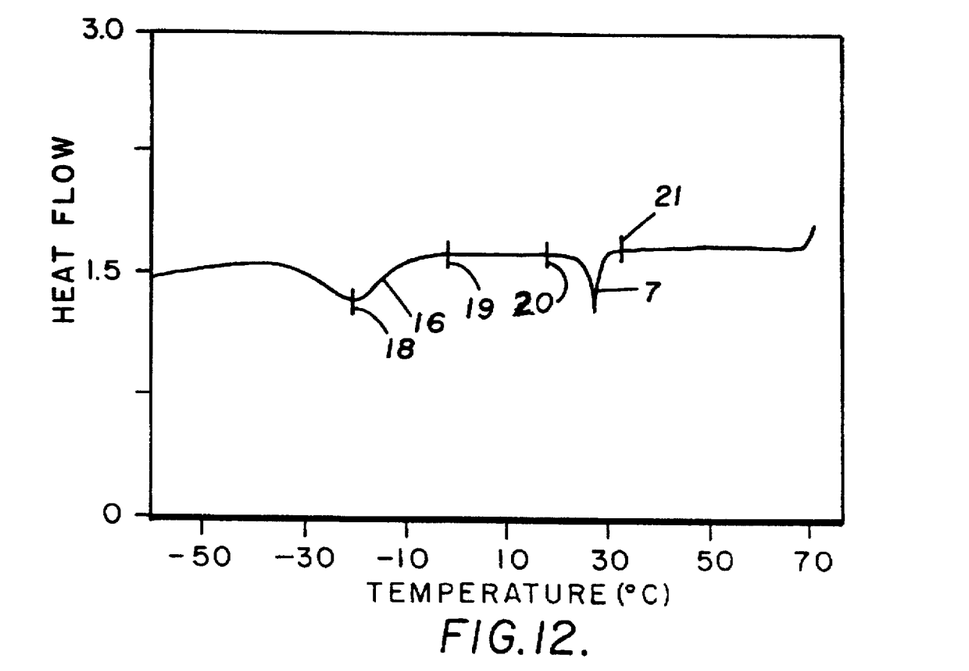
FIG. 12 Shows that the 4.8% stearic acid portion of a molten mixture with alachlor crystallized at about 29° C., and then a portion of the supercooled alachlor crystallized at about –13° C.
Figure 13:
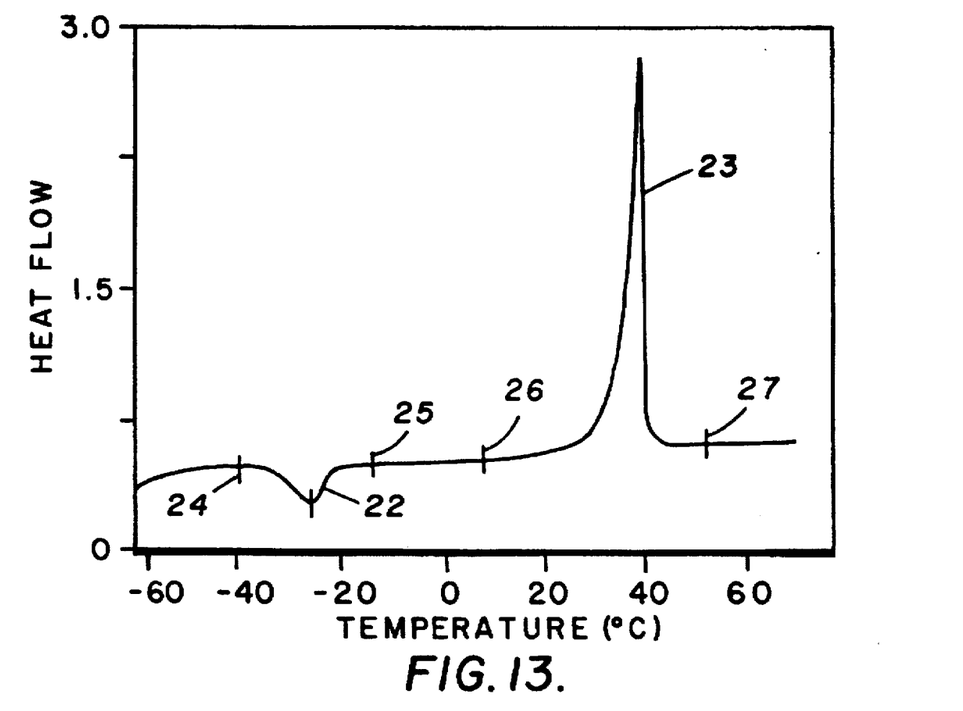
FIG. 13 Shows that the sample with crystalline stearic acid, some crystalline alachlor, and some supercooled alachlor, crystallized further at about –32° C., and then fully melted at about 35° C.

Results:

1. During cool-down and heat-up, no melting or crystallization occurred. Technical remained supercooled. See FIG. 11.
2. Stearic acid crystallized on cool-down, followed by a portion of the alachlor crystallizing at −−15° C. On heat-up, more alachlor crystallized, followed by melting of alachlor and stearic acid as one component. See FIG. 12 and FIG. 13.

Here, alachlor technical was nucleated by a select compound from the above group, stearic acid, causing alachlor crystallization.

Biological Activity

While evaluating the economic position of WP, WG, and SC formulations, one would compare the unit activity of formulations of this invention against an organic solvent-based formulation, such as an emulsifiable concentrate (EC). Some compositions of this invention have been used to kill or control weeds (pests) using standard testing procedures employing the application of a pesticidally effective amount of a formulation of this invention containing a pesticide active to a pest in an acceptable agronomic method. Observations of the effect of such application over time showed the pesticidal effect as kill or control of the weed (pest).

Figure 14:
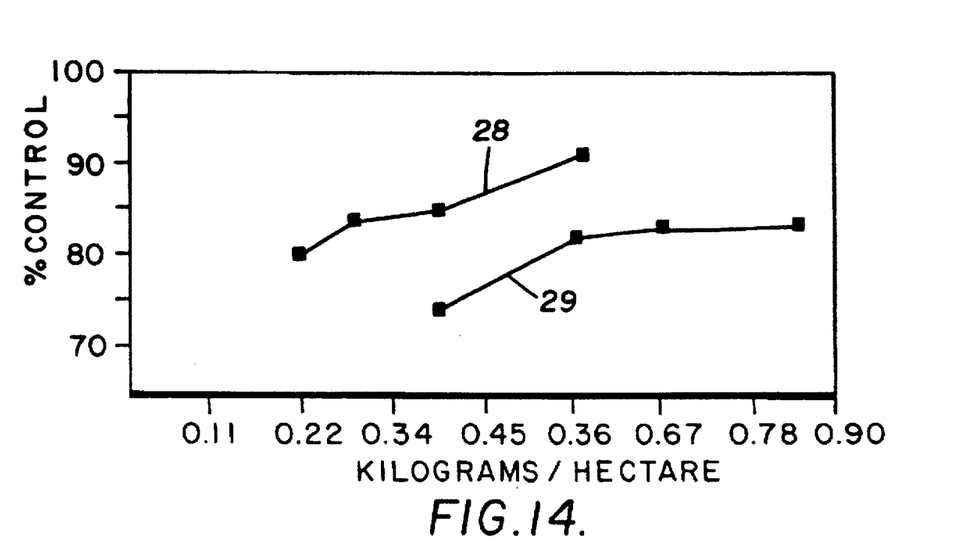
FIG. 14 Shows that a dithiopyr sprayable formulation, based on stearic acid as nucleating agent, had greater efficacy on weeds than the EC sprayable formulation.

A water-dispersible formulation of dithiopyr, utilizing stearic acid as nucleating agent, was compared to the commercial EC formulation in several field trials. See FIG. 14. As shown, the mean unit activity of the dispersible formulation in fact exceeded that of the EC. This dispersible formulation had the following approximate composition:

| | Ingredient | Approximate Weight % |
| --- | --- | --- |
| HiSil ABS | (Silica, precipitated) | 36 |
| | Dithiopyr Technical | 40 |
| Hystrene 9718 | (stearic acid) | 12 |
| Stepanol ME Dry | (lauryl sulfate salt) | 5 |
| Darvan 404 | (lignosulfonate salt) | 5 |
| Agrimer 30 | (polyvinylpyrolidone) | 2 |

It is to be understood that the present invention is not limited to the specific embodiments shown and described herein, but may be carried out in other ways without departure from its spirit or scope. All parts are by weight herein unless otherwise specified.

What is claimed is:

1. An aqueous, stable pesticidal suspension which comprises:

a low melting temperature pesticide active ingredient;

a nucleating agent selected from the group consisting of carboxylic acids, esters, and amides having a melting point in the range from about 30° to about 130° and having a chain length in the range from about 3 to about 30;

water; and a plurality of porous carrier particles dispersed in said water, said particles having mean size in the range from 2 to 20 μm, said active ingredients being crystallized in said porous carrier particles and said active ingredient containing said nucleating agent.

2. The suspension of claim 1 wherein said low meting temperature pesticide active ingredient has a melting point in the range from about 30° C. to about 130° C. at normal atmospheric pressure.

3. The suspension of claim 1 wherein said low melting temperature pesticide active ingredient has a melting point in the range from about 30° C. to about 90° C. at normal atmospheric pressure.

4. The suspension of claim 1 wherein said active ingredient is selected from the group consisting of pyridines, nitroanilines, acetanilides, organophosphates, triazines, pyrethroids, isoazolidinones, carbamates, benzoxazoles, substituted phenoxys, substituted ureas, triazoles, oxadiazolinones imidazolinones, azoryls, mixtures thereof.

5. The suspension of claim 1 wherein said active ingredient is dithiopyr and said nucleating agent has a chain length in the range from about 5 to about 22 carbon atoms.

6. The suspension of claim 1 wherein said active ingredient is selected from the group consisting of alachlor, chlorpyrifos, ametryn, bifenthrin, clomazone, triallate, fenoxaprop-ethyl, diclofop-methyl, fenoxycarb, thiazopyr, oxyfluorofen, linuron, imibenconazole, oxadiazon and mixtures thereof.

7. The suspension of claim 1 wherein said nucleating agent is selected from the group consisting of stearic acid, glutaric acid, methyl behenate, stearamide and mixtures thereof.

8. The suspension of claim 4 wherein said nucleating agent is stearic acid.

9. The suspension of claim 6 wherein said nucleating agent is stearic acid.

10. The suspension of claim 7 wherein said active ingredient is trifluralin.

11. The suspension of claim 10 wherein said nucleating agent is stearic acid.

12. The suspension of claim 7 wherein said active ingredient is alachlor.

13. The suspension of claim 12 wherein said nucleating agent is stearic acid.

14. A porous carrier composition containing a low melting pesticide, said composition comprising:

a pesticide having a low melting temperature;

a nucleating agent selected from the group consisting of carboxylic acids, esters and amides, said agent having a melting point in the range from about 30° to about 130° C. and having a chain length in the range from about 3 to about 30; and, a plurality of porous carriers, said pesticide being in crystallized form in said porous carrier, said crystallized pesticide containing said nucleating agent.

15. The composition of claim 14 wherein said pesticide has a melting point in the range from about 30° C. to about 130° C. at normal atmospheric pressure.

16. The composition of claim 14 wherein said pesticide has a melting point in the range from about 30° C. to about 90° C. at normal atmospheric pressure.

17. The composition of claim 14 wherein said pesticide is selected from the group consisting of pyridines, nitroanilines, acetanilides, organophosphates, triazines, pyrethroids, isoazolidinones, carbamates, benzoxazoles, substituted phenoxys, substituted ureas, triazoles, oxadiazolinones, imidazolinones, azoryls, mixtures thereof.

18. The composition of claim 14 wherein said pesticide is dithiopyr and said nucleating agent has a chain length in the range from about 5 to about 22 carbon atoms.

19. The composition of claim 14 wherein said pesticide is selected from the group consisting of alachlor, chloropyrifos, ametryn, bifenthrin, clomazone, triallate, fenoxaprop-ethyl, diclofop-methyl, fenoxycarb, thiazopyr, oxyfluorofen, linuron, imibenconazole, oxadiazon and mixtures thereof.

20. The composition of claim 14 wherein said nucleating agent is selected from the group consisting of stearic acid, glutaric acid, methyl behenate, stearamide and mixtures thereof.

21. The composition of claim 14 wherein said nucleating agent is stearic acid.

22. The composition of claim 17 wherein said nucleating agent is stearic acid.

23. The composition of claim 19 wherein said active ingredient is trifluralin.

24. The composition of claim 23 wherein said nucleating agent is stearic acid.

25. The composition of claim 19 wherein said active ingredient is alachlor.

26. The composition of claim 25 wherein said nucleating agent is stearic acid.

27. A suspendable water-dispersible composition containing a low melting temperature pesticide, said composition comprising:
 a plurality of porous carrier particles, said particles having mean size from 2 to 20 µm; p1 a low melting temperature pesiticide, said pesticide being crystallized in said porous carrier particles;
 a nucleating agent in said pesticide, said nucleating agent selected from the group consisting of carboxylic acids, esters and amides, said agents having a melting point in the range from about 30° to about 130° C. and having a chain length in the range from about 3 to about 30.

28. The composition of claim 27 wherein said pesticide has a melting point in the range from about 30° C. to about 130° C. at normal atmospheric pressure.

29. The composition of claim 27 wherein said pesticide has a melting point in the range from about 30° C. to about 90° C. at normal atmospheric pressure.

30. The composition of claim 27 wherein said pesticide is selected from the group consisting of pyridines, nitroanilines, acetanilides, organophosphates, triazines, pyrethroids, isoazolidinones, carbamates, benzoxazoles, substituted phenoxys, substituted ureas, triazoles, oxadiazolinones, imidazolinones, azoryls, mixtures thereof and the like.

31. The composition of claim 27 wherein said pesticide is dithiopyr and said nucleating agent has a chain length in the range from about 5 to about 22 carbon atoms.

32. The composition of claim 27 wherein said active ingredient is selected from the group consisting of alachlor, chlorpyrifos, ametryn, bifenthrin, clomazone, triallate, fenoxaprop-ethyl, diclofop-methyl, fenoxycarb, thiazopyr, oxyfluorofen, linuron, imibenconazole, oxdiazon and mixtures thereof.

33. The composition of claim 32 wherein said nucleating agent is selected from the group consisting of stearic acid, glutaric acid, methyl behenate, stearamide and mixtures thereof.

34. The composition of claim 32 wherein said nucleating agent is stearic acid.

35. The composition of claim 32 wherein said nucleating agent is stearic acid.

36. The composition of claim 32 wherein said active ingredient is trifluralin.

37. The composition of claim 36 wherein said nucleating agent is stearic acid.

38. The composition of claim 32 wherein said active ingredient is alachlor.

39. The composition of claim 38 wherein said nucleating agent is stearic acid.

* * * * *